United States Patent

Behrend et al.

[11] Patent Number: 5,098,991
[45] Date of Patent: Mar. 24, 1992

[54] PROCESS OF PREPARING POLYAMIDE-IMIDE AND POLYIMIDE POLYMERS FROM ACID ANHYDRIDES AND DIANHYDRIDES OF DISUBSTITUTED MALEIC ANHYDRIDES

[75] Inventors: Steven J. Behrend, Naperville; David A. Young, Warrenville; Ellis K. Fields, River Forest, all of Ill.

[73] Assignee: Amoco Corporation, Chicago, Ill.

[21] Appl. No.: 461,733

[22] Filed: Jan. 8, 1990

Related U.S. Application Data

[62] Division of Ser. No. 342,228, Apr. 24, 1989, abandoned.

[51] Int. Cl.⁵ .................. C08G 73/14; C07D 493/04
[52] U.S. Cl. .................................... 528/350; 528/176; 528/179; 528/182; 528/183; 528/188; 528/345; 528/353; 549/232; 549/241

[58] Field of Search ............... 528/176, 183, 188, 182, 528/179, 345, 350, 353

[56] References Cited

U.S. PATENT DOCUMENTS 4,596,867 6/1986 Fields et al. ...................... 528/188
5,003,085 3/1991 Behrend et al. .................. 549/241

Primary Examiner—John Kight, III
Assistant Examiner—P. Hampton-Hightower
Attorney, Agent, or Firm—Gunar J. Blumberg; William H. Magidson; Ralph C. Medhurst

[57] ABSTRACT

A process is disclosed for preparation of anhydrides containing additional carboxylic acid moieties and dianhydrides of disubstituted maleic anhydride compounds wherein the acid anhydrides and dianhydrides retain their alkene character. The resulting alkene compounds are useful as precursors for polyesters, thermally stable polyamide-imides and polyimides which are also disclosed, as well as a process for their preparation.

7 Claims, No Drawings

PROCESS OF PREPARING POLYAMIDE-IMIDE AND POLYIMIDE POLYMERS FROM ACID ANHYDRIDES AND DIANHYDRIDES OF DISUBSTITUTED MALEIC ANHYDRIDES

This is a division of application Ser. No. 342,228, filed Apr. 24, 1989 now abandoned.

FIELD OF THE INVENTION

This invention relates to anhydrides containing additional carboxylic acid moieties and dianhydrides of dissubstituted maleic anhydrides and to a method for their preparation in high yields by oxidation of the di-substituted maleic anhydrides. This novel process for high yield oxidation of disubstituted maleic anhydrides utilizes a cobalt-manganese-bromine catalyst in a reaction medium comprising an aliphatic saturated carboxylic acid of from 2 to 4 carbon atoms, preferably acetic acid or propionic acid, more preferably acetic acid. The novel acid anhydrides and dianhydrides of disubstituted maleic anhydride are useful as precursors for polyesters, thermally stable polyamide-imides and polyimides. Dielectric properties of polyimide films prepared from these novel compounds make these films suitable for electronic applications.

BACKGROUND OF THE INVENTION

It is known to make anhydrides containing additional carboxylic acid moieties and dianhydrides of disubstituted maleic anhydrides by synthesis from simpler compounds. These are disclosed in commonly-assigned U.S. Pat. Nos. 4,596,867 and 4,638,072, which are hereby incorporated by reference. It is also known to make polyimides from dianhydrides and aromatic amines. This is disclosed in U.S. Pat. No. 3,179,634 (1965). British Patent Specification No. 570,858 disclosed various processes for making fiber-forming polymers.

In reviewing these references it is clear that the preparation of anhydrides containing additional carboxylic acid moieties and dianhydrides of disubstituted maleic anhydrides by oxidation of substituted alkenes, i.e., diaryl maleic anhydrides, while retaining their alkene character, has not been contemplated in the prior art. Also, the prior art has not contemplated the preparation of disubstituted maleic anhydride compounds of the structure:

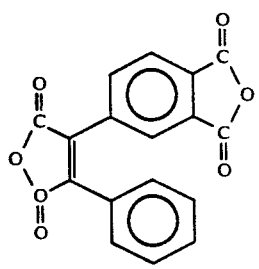

2-(3',4'-phthalic anhydride)-3-phenyl maleic anhydride

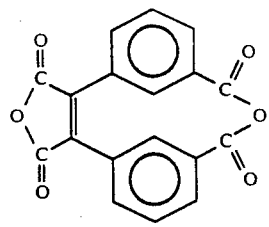

2,3-di(3'-carboxy-phenyl anhydride) maleic anhydride

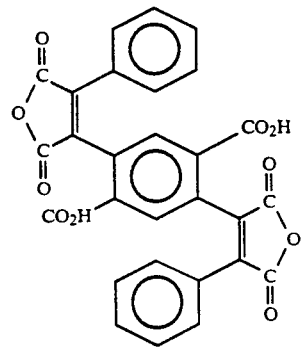

1,4-(2,5-dicarboxy) phenylene bis-phenyl maleic anhydride

The general object of this invention is to provide novel compounds of maleic anhydride structure and novel derivatives of these compounds which are potentially difunctional in structure and to provide novel amide-imide polymers and polyimides. A more specific object of this invention is to provide amide-imide polymers, vinyl polymers, and polyimides from 2-(3',4'-phthalic anhydride)-3phenyl maleic anhydride, 2,3-di(3-carboxyphenyl anhydride) maleic anhydride, and 1,4-(2,5-dicarboxy) phenylene bisphenyl maleic anhydride.

SUMMARY OF THE INVENTION

This invention relates to anhydrides containing additional carboxylic acid moieties and dianhydrides of disubstituted maleic anhydride prepared by the oxidation of disubstituted maleic anhydride compounds. The invention also relates to amide-imide polymers, and polyimides prepared from these maleic anhydride compounds and the methods of preparation thereof.

DETAILS OF THE INVENTION

The invention relates to disubstituted maleic anhydride compounds prepared by the oxidation of maleic anhydride compounds in the presence of a cobalt-manganesebromine catalyst. The structure of these compounds is as follows:

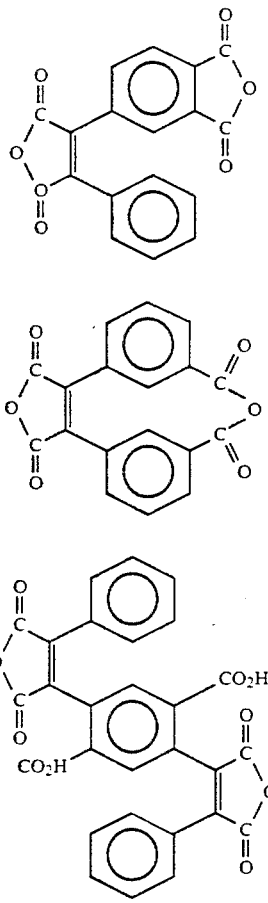

The discoveries associated with the present invention and the objects achieved in accordance with the invention as described herein, include the following: a process of catalytic oxidation by molecular oxygen of aromatic organic compounds containing at least one and preferably a plurality of aliphatic substituents in the conjoint presence of a metal and bromine to produce acid anhydride and dianhydrides of disubstituted maleic anhydride compounds; a process for catalytic oxidation in liquid phase by means of molecular oxygen of disubstituted maleic anhydride compounds having at least one and preferably a plurality of substituents wherein the carbon atom attached directly to the disubstituted maleic anhydride contains at least one hydrogen or oxygen atom in the conjoint presence of metal or metal ions and bromine or bromine ions; such processes wherein the metal is a heavy metal; such processes wherein at least one aliphatic substituent contains from 1 to 4 carbon atoms per aromatic nuclear carbon atom to which it is attached; such processes carried out in the presence of an acid, such as for example, a lower aliphatic mono carboxylic acid containing 1 to 8 carbon atoms in the molecule, said acid being in liquid phase, and preferably being saturated and containing 2–4 carbon atoms in the molecule and preferably employing about 0.1–10 parts by weight of such acid per part by weight of aliphatic substituted aromatic compound; such processes wherein the catalyst is manganese bromide or cobalt bromide or combinations thereof; such processes wherein the catalyst is provided as a mixture of a lower aliphatic carboxylate salt of the desired metal and a bromide or bromate; such processes applied specifically to disubstituted maleic anhydrides wherein each aromatic substituent contains 6 to 20 carbon atoms; and other such processes and modifications thereof as will be apparent as details or embodiments of the invention are set forth hereinafter.

In the practice of the invention, the oxidation of organic compounds whereby corresponding acid anhydrides and dianhydrides of disubstituted maleic anhydrides are obtained, may be effected by reacting such compounds with molecular oxygen, e.g. air, in the conjoint presence of catalytic amounts of a metal and of bromine. Metals of the group of heavy metals shown in the "Periodic Chart of Elements" appearing on pages 60 and 61 of the "Handbook of Chemistry," 10th edition, published by McGraw-Hill Book Company, New York, N.Y. 1967, have been found desirably applicable to this invention for furnishing the metal or metal ion portion of the metal-bromine catalyst. Of the heavy metal group, those metals having an atomic number not greater than 84 have been found most suitable. However, as will appear, metals outside the heavy metal group may also be employed. We have also found that excellent results are obtained by the utilization of a metal having an atomic number 23–28, inclusive. Particularly excellent results are obtained with a metal of the group consisting of manganese, cobalt, nickel, chromium, vanadium, molybdenum, tungsten, tin and cerium. It has also been found that the catalytic amount of the metal may be either as a single metal or as a combination of such metals. The metal may be added in elemental, combined or ionic form and the bromine may be added similarly in elemental, combined or ionic form. As a source of ionic bromine, ammonium bromide or other bromine compounds soluble in the reaction medium may be employed. Satisfactory results have been obtained, for example, with potassium bromate, tetrabromoethane and benzyl bromide.

The metal may be supplied in the form of metal salts. For example, the metal manganese may be supplied as the manganese salt of a lower aliphatic carboxylic acid, such as manganese acetate, in the form of an organic complex, of which mention may be made of the acetylacetonate, the 8-hydroxy-quinolinate and the ethylene diamine tetra-acetate, as well as manganese salts such as the borates, halides and nitrates which are also efficacious.

The reaction temperature should be sufficiently high so that the desired oxidation reaction occurs, and yet not so high as to cause undesirable charring or formation of tars. Thus, temperatures in the range of 120 to 275° C., desirably 150 to 250° C., and preferably 160 to 225° C. may be employed. The reaction time should be sufficient to obtain a desirable conversion of the di-substituted maleic anhydride to the desired acid anhydride or di-anhydride compound, e.g., in the range of about 0.5 to 25 or more hours, preferably up to about 4 hours.

The oxygen used may be in the form of substantially 100% oxygen gas or in the form of gaseous mixtures containing lower concentrations of oxygen, such as, for example, air. The ratio of total oxygen fed into the reaction mixture relative to the hydrocarbon is in the range of about 2 to 500 mols of oxygen per mol of substituted aromatic material, desirably in the range of 5 to 300, and preferably in the range of 5 to 75.

The process of the present invention should be conducted under essentially liquid phase conditions wherein a liquid phase is maintained in the reaction zone. Thus, the feed is not substantially vaporized. The relation of temperature and pressure should be so regulated as to provide a liquid phase in the reaction zone. Generally, the pressure may be in the range of atmospheric up to about 1500 psig. The liquid phase may comprise all or a portion of the organic reactant or it may comprise a reaction medium in which the organic reactant is soluble or suspended.

When the conditions are such that the desired product may be obtained and readily separated from the reaction mixture in the absence of additional reaction medium, such added medium is not required. However, where all such conditions do not obtain or where the presence of an added reaction medium is desired to facilitate carrying out the desired reaction or recovering the desired product or products, an added medium may be included. This added medium may be, and often desirably is, a monocarboxylic acid relatively stable or inert to oxidation in the reaction system, preferably containing about 1 to 8 carbon atoms in the molecule. Saturated aliphatic acids containing 2 to 4 carbon atoms in the molecule and free of hydrogen atoms attached to tertiary carbon atoms are particularly preferred. Where all the advantages of an acid medium are not required, other inert media can be used.

Where the lower aliphatic monocarboxylic acid medium is used, it is generally not necessary to use large amounts thereof. Such acids in the range of 0.1 to 10 parts by weight, desirably 0.5 to 4, and preferably 1 to 2.5 per part of the aromatic material, have been found adequate.

The catalyst illustratively, may be manganese bromide, and it may be added as such or by means of materials which provide a catalytic amount of manganese and of bromine in the reaction system. Manganese may be added in the form of the metal, oxide or acetate or analogous carboxylate salts including a salt of a carboxylic acid which may be formed in the reaction system or as a manganese halide; and the bromine may, as above indicated, be added in the form of elemental bromine, as ammonium bromide or other bromine compounds soluble in the system, e.g. potassium bromate. If desired, the bromine may be in the form of a soluble organic bromide, viz. tetrabromoethene, benzyl bromide, and the like. The amount of the catalyst calculated as $MnBr_2$ may be in the range of about 0.1 to 10 percent by weight or more of the reactant charged, desirably 0.3 to 2, and preferably 0.5 to 1.7 percent. Mixtures of materials may be used; and the proportions of manganese and bromine may be varied from their stoichiometric proportions encountered in $MnBr_2$, e.g., in the range of about 1 to 7 atoms of manganese per atom of bromine, and about 1 to 10 atoms of bromine per atom of manganese. Moreover, the manganese may, as above indicated, be utilized in the form of an organic complex by way of example as the acetylacetonate, the 8-hydroxy quinolinate, and the ethylene diamine tetra acetate of manganese.

Novel amide-imide polymers and polyimide polymers have been prepared from the acid anhydrides and dianhydrides of disubstituted maleic anhydride compounds by a simple condensation reaction with a difunctional amine and requiring only the application of heat. Temperature range is from about 80° C. to about 250° C., preferably from about 160° C. to about 220° C.

The polymers of this invention have outstanding resistance to heat and solvents, high mechanical strength and excellent electrical properties.

The polymers of this invention are formed by reacting the anhydride-acids and dianhydrides of this invention with a difunctional amine of the general formula $NH_2—NH^8—NH_2$ wherein $R^8$ is selected from the group consisting of $—R^6—$ and $—R^6—X—R^7—$ wherein $R^6$ and $R^7$ are individually selected from divalent groups selected from the group consisting of from 2 to 20 methylene groups and 1 to 3 phenylene groups and X is selected from the group consisting of $—O—$, $—S—$, $—SO_2—$ and $—CH_2$.

It is known that the reaction between the difunctional amine and the anhydride can be carried out either in bulk or in an inert polar carrier medium. In the bulk process, apparently because reactivity is low unless the mixture is melted, it is necessary to heat the reaction mixture to an elevated temperature on the order of 100° C. to 200° C. to induce any reaction at all between the two reagents. In most cases, at least about 120° C. is used and it is preferred to heat at about 160° C. if the reaction is to be comprised in a reasonable time. If an inert polar carrier medium is to be used, it is preferred that N-methylpyrrolidinone (NMP) be employed. Dimethylacetamide, dimethylformamide, and a pyridine:toluene 50:50 mixture can also be used. If N-methylpyrrolidinone (NMP) is used as a carrier, it is specifically recommended to heat the solution at reflux temperature, i.e., near 202° C.

It is known that production of the imide by reaction of a diamine with an anhydride is accompanied by the formation of water. The water of reaction can be removed by addition of an aromatic compound such as xylene or toluene which forms an azeotrope with water which can then be distilled. Other side reaction products can be removed by precipitation of the imide and other separation techniques.

The process by which novel polymer compositions of this invention are prepared comprises (a) dissolving a difunctional amine and the maleic anhydride compound in an inert solvent to form a solution containing about 1 mole of anhydride for each mole of amine, (b) heating the solution at a temperature not in excess of 250° C. to form a condensation product in which the amine groups have substantially reacted. Conventional product separation techniques are used to obtain and purify the resulting polymer.

Under preferred conditions of the oxidation process, the reaction medium comprises an aliphatic saturated carboxylic acid of from 2 to 4 carbon atoms, preferably acetic acid or propionic acid, more preferably acetic acid. It is further preferable that the carboxylic acid be present in an initial ratio of at least 1.8:1 to 20:1, upon a weight basis, of the starting weight of said disubstituted maleic anhydride compound and that the final weight ratio of acid to said disubstituted maleic anhydride compound be from 1.5:1 to 2.0:1.

In particular, this invention is a process for the oxidation of substituted alkenes. The catalyst can comprise cobalt acetate, manganese diacetate, and sodium bromide in a 1:1:2 mole ratio.

The process can be conducted in a batch, continuous or semi-continuous method.

The process can be conducted batchwise as follows: the starting compound, the acetic acid solvent, and the catalyst components are introduced into a stirred titanium-clad autoclave. Oxygen or air is fed continuously through an air inlet.

In a continuous process, the reaction is conducted in a reactor provided with a column for refluxing into which the starting material, acetic acid, catalyst and oxygen, or air, are introduced continuously, and from which a portion of the reaction mixture is continuously withdrawn and passed to a filter centrifuge for recovery. The mother liquor is continuously recycled to the reactor.

In a specific embodiment, all components are charged to the reactor at or near oxidation initiation temperature, preferably at about 150° C. to about 250° C. and at a pressure to maintain liquid-phase conditions. Then pressurized air is injected into the reaction mixture and the reaction temperature is permitted to increase by heat evolved by the oxidation reaction to about 160° C.-250° C. but not to exceed about 275° C.

The total bromine can be from a single source of bromine, for example, ionic bromine sources (HBr, NaBr, NH Br, and the like) or from a combined form of bromine, for example, organic bromides such as benzylbromide, tetrabromoethane and others. An ionic form of bromine is preferred.

The catalyst can comprise a cobalt(II) compound, a manganese(II) compound, and a bromine compound. Based upon the weight of the substrate to be oxidized, cobalt is percent in an amount of from about 0.5 to 0.7 weight percent, manganese is present in an amount of from about 0.3 to 0.5 weight percent, and bromine is present in a weight ratio to the substrate of about 0.10 to about 0.30 weight percent and total weight ratio of bromine ions to total metal ions of cobalt and manganese is from about 0.7 to about 2.0. The carboxylic acid can be selected from acetic acid and propionic acid. Acetic acid is preferred. The source of molecular oxygen preferably is air. In a specific application the molecular oxygen comprises air, the solvent comprises acetic acid, the said catalyst comprises cobalt and manganese in a mole ratio of 1:1, bromine is present in a weight ratio to disubstituted maleic anhydride compound of 0.10 to 0.30; process temperature is in the range of from about 150° C. to about 250° C. and pressure is in the range of from about atmospheric to about 1500 psig, preferably from 125 psig to about 500 psig.

In summary, the instant invention comprises a process for preparation of acid anhydrides and dianhydrides of disubstituted maleic anhydrides by oxidation of the corresponding disubstituted maleic anhydride which comprises reacting in a reaction zone a disubstituted maleic anhydride thereof with molecular oxygen in the presence of a catalyst comprising in conjoint presence bromine and a heavy metal oxidation catalyst, and recovering said acid anhydrides and dianhydrides of said disubstituted maleic anhydrides.

In more detail, said heavy metal of said catalyst is preferably in ionic form, said bromine is preferably in ionic form and said heavy metal has an atomic number of from 23 to 28 inclusive. In further detail, the heavy metal can be selected from the group consisting of manganese, cobalt, nickel, chromium, vanadium, molybdenum, tungsten, tin, cerium and combinations thereof. The heavy metal can comprise manganese, or can comprise manganese and cobalt. The process can be carried out in the presence of a mono-carboxylic acid having 1 to 8 carbon atoms in the molecule. Most preferably, the monocarboxylic acid is acetic acid, process temperature is in the range of from about 120° C. to about 275° C. and pressure is in the range of from about 125 psig to about 500 psig.

The invention also comprises a process for preparation of amide-imide polymers and polyimide polymers which comprises reacting acid anhydrides and dianhydrides of disubstituted maleic anhydrides with a difunctional amine of the formula $NH_2—R^8—NH_2$ wherein $R^8$ is selected from the group consisting of $—R^6—$ and $—R^6—X—R^7—$ wherein $R^6$ and $R^{b\ 7}$ are individually selected from divalent groups selected from the group consisting of from 2 to 20 methylene groups and 1 to 3 phenylene groups, and X is selected from the group consisting of $—O—$, $—S—$, $—SO_2—$ and $—CH_2$, at a temperature within the range of from about 80° C. to about 250° C. and at a pressure within the range of from about 125 psig to about 500 psig.

The invention further comprises the composition produced by reacting acid anhydrides and dianhydrides of disubstituted maleic anhydrides with difunctional amines as previously described. In particular, the compositions are the reaction products of 2,3-di(3-carboxyphenyl anhydride) maleic anhydride and 4,4'-oxybisaniline; 2-(3',4'phthalic anhydride) -3- phenyl maleic anhydride and 4,4'-oxybisaniline; and 1,4-(2,5-dicarboxy) phenylene bisphenyl maleic anhydride and hexamethylene diamine. In more detail, the reaction for preparing the amide-imide polymers and polyimide polymers can be in the presence of an inert polar medium. The inert polar medium can be selected from the group consisting of N-methylpyrrolidinone, dimethylacetamide, dimethylformamide, and pyridine in a 50:50 mixture with toluene.

The novel process is exemplified by the following examples. These examples are exemplary only and are not meant to be construed as limiting.

EXAMPLE I

A one liter titanium stirred autoclave equipped with a condenser, air, and nitrogen gas inlets was charged with 50.03 grams (0.180 moles) of 2-(3',4'-dimethylphenyl)-3phenyl maleic anhydride dissolved in 450.10 grams glacial acetic acid containing a catalyst mixture comprised of 1.37 grams 48% aqueous HBr, 1.00 gram cobalt (II) acetate, and 1.00 gram manganese (II) acetate. The sealed autoclave was pressurized with 250 psig of nitrogen and heated with stirring to a temperature of 162° C. whereupon air (17.9% oxygen in nitrogen) was introduced at a flow rate of 10 SCFH at a pressure of 250 psig. A mild exotherm accompanied the gradual uptake of $O_2$ as the oxidation initiated. Air pressure was increased to 300 psig 20 minutes after the introduction of air to prevent loss of acetic acid. The temperature range maintained by heating and heat of reaction during the course of the oxidation was 162-195° C. By the end of 30 minutes an $O_2$ reading of 17.7% indicating completion of the oxidation reaction, was observed. No significant amount of CO or $CO_2$ was generated during oxidation. GC analysis of the reaction mixture (a clear yellow-brown colored solution) showed the presence of starting material and 2-(3',4'-phthalic anhydride)-3-phenyl maleic anhydride. Dilution of the reaction mixture with 1.5 liters of water induced precipitation of the above dianhydride as a light yellow colored solid. Recrystallization of the dianhydride from acetic anhydride gave a crystalline pale yellow solid with a melting point of 155-156° C.; IR $\nu(CO)$, 1850 cm$^{-1}$(m), 1760 cm$^{-1}$(s). $^1$H NMR (in acetone $d_6$) shows only aromatic protons.

EXAMPLE II

In this case, the same autoclave and essentially the same conditions were employed as in Example I with the following exceptions. 75.01 grams (0.270 moles) of 2-(3',4'-dimethylphenyl)-3-phenyl maleic anhydride and an addition to the catalyst mixture of 0.13 grams zirconium (IV) diacetate oxide in a total of 400.0 grams glacial acetic acid containing 47.9 grams of water were used. The temperature range during the course of the oxidation was 160° (initial) to 201° C. Air pressure was kept between 250 to 380 psig. A very small amount of CO and $CO_2$ was observed during oxidation. Dilution of the lighter colored reaction mixture with water (as in Example I) caused precipitation of 2-(3',4'-phthalic acid)-3-phenyl maleic anhydride. Recrystallization from ethanol gave a pale yellow solid with a melting point of 194-196° C. (dec.), IR $\nu$(CO), 1830 cm$^{-1}$(m), 1760 cm$^{-1}$(ms), and 1700 cm$^{-1}$(s).

EXAMPLE III

Reactor, starting materials (including catalyst mixture), and quantities were identical to those in Example II with the exception of the deletion of water and the addition of 25.0 grams acetic anhydride. The product isolated in this example was 2-(3',4'-phthalic anhydride)-3-phenyl maleic anhydride just as in Example I.

GC Yields for the products of Examples I-III were in the 85-95% range.

EXAMPLE IV

The following illustrates the preparation of 2,3-di(3'-carboxyphenyl anhydride( maleic anhydride.

A one-liter titanium, stirred autoclave equipped with a condenser, air and nitrogen gas inlets was charged with 25.05 grams (0.090 moles) of 2,3-di(m-tolyl) maleic anhydride dissolved in 300 grams of glacial acetic acid containing a catalyst mixture comprised of 1.37 grams 48% aqueous HBr, 1.00 grams cobalt (II) acetate, 1.00 grams manganese (II) acetate and 0.13 grams zirconium (IV) diacetate oxide. The sealed autoclave was pressurized with 250 psig of nitrogen and heated with stirring to 175° C. whereupon air (17.9% oxygen in nitrogen) was introduced at a flow rate of 15 SCFH at a pressure of 350 psig. A mild exotherm ensued with the gradual uptake of oxygen as the oxidation initiated.

Air pressure was increased to 450 psig 30 minutes after the introduction of air to prevent loss of acetic acid. The temperature range was maintained by heating and the heat of reaction during the course of the oxidation within the range of 175° C. to 210° C. An oxidation reading of 17.2% was observed after 60 minutes and the reaction was terminated. Small amounts of $CO_2$ were generated; however no significant amount of CO was observed. A 76% yield of the pale yellow dicarboxylic acid was recovered from the reaction mixture by filtration. The crude product decomposed at a temperature greater than 320° C. with elimination of water, presumably dehydrating to the dianhydride. Infrared absorption for the carbonyl band was 1820 cm$^{-1}$ (medium), 1760 cm$^{-1}$ (strong), 1680 cm$^{-1}$ (strong). High resolution probe mass spectrometry analysis gave the correct molecular weight of 338 and a fragmentation pattern consistent with the dicarboxylic acid structure. Isophthalic acid was also observed as a very minor byproduct. Recrystallization of the dicarboxylic acid from hot acetic anhydride yielded pale yellow-green colored crystals of the novel 12 carbon ring dianhydride, 2,3-di(3'-carboxyphenyl anhydride) maleic anhydride, with a melting point of 395-397° C., infrared absorption for the carbonyl band was 1810 cm$^{-1}$ (weak), 1770 cm$^{-1}$ (strong), 1725 cm$^{-1}$ (weak).

EXAMPLE V

A dried 50ml three-neck round-bottomed flask equipped with a condenser, drying tube, magnetic stirring bar, and a nitrogen gas inlet was charged with 2.00g (0.01 mol) of 4,4'-oxybisaniline and 10ml of 1-methyl-2-pyrrolidinone. 3.20g (0.01 mol) of 2,3-di(3'-carboxyphenyl anhydride) maleic anhydride, mp 395-7° C., was then added to the magnetically-stirred 4,4'-oxybisaniline solution along with an additional 6ml of 1-methyl-2-pyrrolidinone to complete the transfer. A positive pressure of nitrogen was kept over the reaction and heating was applied after 10 minutes of stirring at room temperature. The temperature of the reaction was gradually raised to 200° C. After 6 hours at 200° C. the resulting yellow-brown solution was cooled and mixed with water in a blender. The precipitated polyimide was filtered, washed with hot water, and oven dried under reduced pressure (80mm) at 220° C. for 16 hours. The polymer has an inherent viscosity of 0.41 and a Tg of 234° C. with a 10% weight loss under a nitrogen atmosphere at 440° C.

What is claimed is:

1. A process for the preparation of amide imide polymers and polyimide polymers which consists essentially of reacting acid anhydrides and dianhydrides of disubstituted maleic anhydrides selected from the group consisting of 2.3-di(3-carboxy-phenyl anhydride) maleic anhydride, 2-(3', 4'-phthalic anhydride)-3-phenyl maleic anhydride and 1,4-(2,5-cicarboxy)phenylene bis-phenyl maleic anhydride with a difunctional amine of the formula $NH_2$—$R^8$—$NH_2$ wherein $R^8$ is selected from the group consisting of —$R^6$— and —$R^6$—X—$R^7$—, wherein $R^6$ and $R^7$ are individually selected from divalent groups selected from groups consisting of from 2 to 20 methylene groups and 1 to 3 phenylene groups, and X is selected from the group consisting of —O—, —S—, —$SO_2$— and—$CH_2$, at a temperature within the range of from about 80° C. to about 250° C. and at a pressure within the range of from 125 psig to about 500 psig.

2. A composition produced according to the process of claim 1.

3. The process of claim 1 wherein said disubstituted maleic anhydride is 2,3-di(3-carboxy-phenyl anhydride) maleic anhydride and said difunctional amine is 4,4'-oxybisaniline.

4. The process of claim 1 wherein said disubstituted maleic anhydride is 2-(3',4'-phthalic anhydride) -3-phenyl maleic anhydride and said difunctional amine is 4,4'-oxybisaniline.

5. The process of claim 1 wherein said disubstituted maleic anhydride is 1,4-(2,5-dicarboxy)phenylene bis-phenyl maleic anhydride and said difunctional amine is hexamethylene diamine.

6. The process of claim 1 wherein said acid anhydrides and dianhydrides of disubstituted maleic anhydride and said difunctional amine are reacted in the presence of an inert polar medium.

7. The process of claim 6 wherein said inert polar medium is selected from the group consisting of N-methylpyrrolidinone, dimethylacetamide, dimethylformamide and pyridine in a 50:50 mixture with toluene.

* * * * *

UNITED STATES PATENT AND TRADEMARK OFFICE
CERTIFICATE OF CORRECTION

PATENT NO. : 5,098,991
DATED : March 24, 1992
INVENTOR(S) : Steven J. Behrend, David A. Young, and Ellis K. Fields It is certified that error appears in the above-indentified patent and that said Letters Patent is hereby corrected as shown below:

| Col. | Line | | |
|---|---|---|---|
| 2 | 44 | "3phenyl meleic anhydride" should read | --3-phenyl maleic anhydride-- |
| 2 | 66 | "cobalt-manganesebromine" should read | --cobalt-manganese-bromine-- |
| 7 | 17 | "NaBr, NH Br," should read | --NaBr, $NH_4Br$-- |
| 7 | 24 | "is percent in an amount" should read | --is present in an amount-- |
| 8 | 5 | "$R^6$ and $R^{b\ 7}$" should read | --$R^6$ and $R^7$-- |
| 8 | 37 | "3phenyl maleic anhydride" should read | --3-phenyl maleic anhydride-- |
| 10 | 26 | "amide imide polymers" should read | --amide-imide polymers-- |
| 10 | 30 | "2.3-di(3-carboxy..." should read | --2,3-di(3-carboxy...-- |

Signed and Sealed this

Twenty-sixth Day of October, 1993

Attest:

BRUCE LEHMAN

Attesting Officer     Commissioner of Patents and Trademarks